United States Patent
Marzaro

(10) Patent No.: US 10,195,307 B2
(45) Date of Patent: Feb. 5, 2019

(54) METHOD FOR PREPARING AN ACELLULAR ORGANIC TISSUE FOR REVITALISATION

(71) Applicant: TELEA BIOTECH S.R.L., Sandrigo (VI) (IT)

(72) Inventor: Maurizio Marzaro, Treviso (IT)

(73) Assignee: Telea Biotech S.R.L., Sandrigo (VI) (IT)

( * ) Notice: Subject to any disclaimer, the term of this patent is extended or adjusted under 35 U.S.C. 154(b) by 0 days.

(21) Appl. No.: 13/780,856

(22) Filed: Feb. 28, 2013

(65) Prior Publication Data

US 2018/0339086 A1  Nov. 29, 2018

Related U.S. Application Data

(62) Division of application No. 12/601,306, filed as application No. PCT/IB2008/000921 on Apr. 16, 2008, now abandoned.

(30) Foreign Application Priority Data

May 31, 2007 (IT) ................ VI2007A0159

(51) Int. Cl.
*C12N 13/00* (2006.01)
*A61L 27/36* (2006.01)
*A61L 27/56* (2006.01)

(52) U.S. Cl.
CPC .......... *A61L 27/3604* (2013.01); *A61L 27/56* (2013.01)

(58) Field of Classification Search
None
See application file for complete search history.

(56) References Cited

U.S. PATENT DOCUMENTS 5,112,354 A * 5/1992 Sires ........................ A61F 2/28
  600/36
7,300,437 B2 * 11/2007 Pozzato ............. A61B 18/1402
  128/898

* cited by examiner

*Primary Examiner* — Robert J Yamasaki
(74) *Attorney, Agent, or Firm* — Workman Nydegger

(57) ABSTRACT

The invention concerns a method for preparing an acellular organic tissue for revitalisation by means of the reimplantation of living cells, said method involving the following stages: preparing the acellular tissue on an essentially flat surface, creating a plurality of holes on the surface of the tissue, distributed all over said surface and positioned so that they penetrate at least through a portion of the thickness of said tissue. The holes are suitable for containing the living cells when they are reimplanted.

18 Claims, 1 Drawing Sheet

US 10,195,307 B2

METHOD FOR PREPARING AN ACELLULAR ORGANIC TISSUE FOR REVITALISATION

CROSS-REFERENCE TO RELATED APPLICATION

This is a divisional of co-pending U.S. patent application Ser. No. 12/601,306, which was filed on Mar. 2, 2010, which in turn was a National Stage filing of International Patent Application No. PCT/IB2008/000921, which was filed on Apr. 16, 2008.

FIELD OF THE INVENTION

The invention relates to a method for preparing an acellular tissue for revitalisation.

BACKGROUND OF THE INVENTION

It is well known in the medical sector, and more specifically in the surgical sector, that it is becoming increasingly important to have tissues available for grafting into living beings to meet the growing need to replace parts of organs or whole organs.

The creation of biological substitutes that are prepared in the laboratory and then transplanted into animal or human recipients is a medical procedure known by the name of "tissue engineering".

According to a known technique, tissues for grafting are prepared in the laboratory by implanting cells into a matrix consisting of an inorganic supporting medium generally called a "scaffold".

The "scaffold", which is used to compensate for a loss of substance of the organ being treated, facilitates the three-dimensional organisation of the cells until the formation of new tissue has been completed.

The scaffold must naturally then undergo a process of degradation until it disappears completely and is replaced by the regenerated tissue, which is facilitated by the cells implanted in said scaffold.

Transplants can be obtained using this method with either artificial or natural scaffolds (i.e. from a "donor") obtainable from humans or animals, such as the oesophageal wall.

To use a natural scaffold harvested from a donor for transplanting into another human being, the tissue must be treated first to eliminate all the cells existing between the fibres of the connective tissue, and then to reimplant human cells belonging to the intended recipient of the graft (the "host") in order to avoid rejection phenomena.

The techniques used to create a scaffold, i.e. an acellular matrix, starting from tissues harvested from a donor, are well known and are consequently not described in detail here; briefly, they involve immerging the tissue to be treated in a fluid containing enzymatic substances capable of digesting and destroying the living cells contained within the tissue without damaging the tissue's connective fibres.

After creating an acellular tissue matrix, ready to receive the cells obtained from the host, said tissue, or scaffold, is prepared in a so-called "Petri dish" (or similar container), which is a tray commonly used in biological laboratories, on the bottom of which the tissue to revitalise is rested.

The tissue is revitalised by implanting stem cells from the future recipient and nourishing them with a cell culture broth that feeds the cells, keeping them alive and enabling them to multiply and become disseminated.

Basically, the stem cells initially placed on the upper surface of the tissue move through the natural interstitia in the tissue of the scaffold—interstitia that were previously occupied by the donor's cells.

After a given period of time, under controlled temperatures and in the presence of the nutritional substances contained in the culture broth, the living cells reposition themselves in the interstitia of the tissue, which is then ready for transplantation into the host organ.

It should be noted that the cells generally used to revitalise the scaffold are stem cells, which subsequently become differentiated (or may have already done so) and acquire the specific function of the organ in which the revitalised tissue is grafted.

The success or failure of the transplantation of the tissue treated in this way depends on a capillary diffusion of the cells through the tissue matrix.

If this diffusion proves difficult or occurs on the surface, but not in depth, the transplanted tissue is not adequately revitalised and a necrotic process begins, leading to the failure of the transplant.

From the above considerations, it is clear that it is essential and important, not to say indispensable to success, to ensure the in-depth revitalisation of every part of the tissue, particularly through its full thickness.

For the time being, even when the preparatory and revitalising treatments are applied for a sufficiently lengthy period of time, it is still impossible to ensure results reliable enough to guarantee against any graft failures.

This is due to the scarce penetration of the living cells being reimplanted in the scaffold.

In practical terms, this drawback considerably restricts the opportunity to prepare tissues suitable for transplantation because thicker tissues are not fully revitalised after the transplant since they cannot be penetrated in sufficient depth.

It is consequently evident that the current technique is only suitable for the transplantation of tissues of very limited thickness, e.g. not exceeding approximately 0.1 mm.

U.S. Pat. No. 5,112,354 discloses the preparation of a bone allograft wherein first all soft tissue is removed and then the surface is textured to produce a pattern of holes adapted to facilitate the demineralization of the bone and to increase the surface for interaction with subsequently introduced mesenchymal cells. The holes are produced by laser or mechanical drilling.

BRIEF SUMMARY OF THE INVENTION

The object of the present invention is to develop a method for preparing acellular tissues that overcomes the above-mentioned drawbacks.

More specifically, the object of the invention is to develop a method for preparing acellular organic tissue so that, when said tissue is revitalised with stem cells, it is easier for said cells to penetrate and colonise every possible space in the network of connective tissue fibres, so as to substantially recreate the same conditions of the tissue before it was devitalised.

Another object of the invention is to obtain a significant and important reduction in the treatment time needed to revitalise the acellular scaffold once the living cells have been added in order to prepare the tissue for transplantation.

The objects of the invention are achieved by a method for preparing an acellular organic tissue according to the contents of claim 1.

More precisely, this method consists in the creation of a plurality of holes in the surface of the tissue being prepared;

these holes penetrate at least through a portion of the thickness, and preferably through the full thickness of the tissue concerned.

These holes are obtained by means of a device containing needles with a suitable current passing therethrough and without inducing any alteration (tearing, necrosis, reduction or increase in thickness, changes in fluid content, or coagulation) in the connective tissue surrounding the hole being created.

The holes can be made through the thickness of the tissue being treated using various devices and methods, provided that the preparation of these holes does not cause any deterioration of the connective tissue surrounding the hole and of the scaffold in general.

According to the description given below, the object of the invention and the best results in qualitative terms for the holes created in the tissue are achieved by applying a high-frequency voltage (generally 4 MHz) to the tip of each needle used to create each hole, so as to induce the passage of a weak electric current, but strong enough to break the bonds between the molecules in the connective tissue, thereby creating a hole, without inducing any breakage of the molecules.

This gives rise to narrow-diameter holes, essentially equating to the gauge of the needle being inserted.

It is important to use needles of very narrow gauge, e.g. in the order of 50 μm, but sufficient to facilitate the penetration of the cells inside said holes to revitalise the surrounding tissue.

It is logical and evident that creating numerous holes means preparing new routes for grafting cells into the deepest parts of the tissue, thus ensuring the complete revitalisation of the tissue concerned.

Using the method according to the invention, there is practically no limit to the thickness of the tissues that can be prepared for transplantation, since the holes can be made throughout the thickness of the tissue and over its entire surface, enabling its complete revitalisation because the living cells reimplanted in the acellular scaffold can penetrate throughout the tissue.

Further characteristics and particular features of the invention will be highlighted in greater detail in the description of a preferred embodiment of the invention, provided here as a non-limiting example, and of a device usable in the method.

BRIEF DESCRIPTION OF THE DRAWINGS

The invention is described below with the aid of the attached drawings, wherein.

DETAILED DESCRIPTION OF THE INVENTION

According to the invention, a previously-treated acellular organic tissue, the so-called scaffold, is deposited on the bottom of a Petri dish (or similar container) so that it lies spread out on a flat surface.

Figure 2:
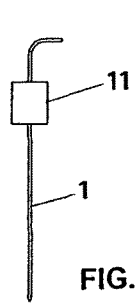
FIG. 2 shows one of the needles in the holder.
Figure 3:
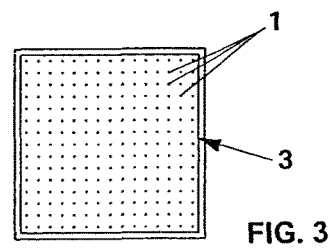
FIG. 3 shows the layout of the array of needles.

A plurality of needles, such as the one indicated by the numeral 1 and shown in FIG. 2, is arranged in an array, e.g. to form a square, indicated as a whole by the numeral 3 in FIG. 3, so as to ensure an orderly arrangement of needles that are preferably separated by the same distance, i.e. they are equidistant from one another.

The head 11 of each needle 1 is connected electrically, e.g. by means of a metal conductor plate 2 attached to the holder 20 of said array of needles.

Said plate 2 is connected to an electric wire 21 that in turn receives the output from a generator 4.

Said generator 4 is a voltage generator, preferably generating 200-230 Volts, but at a wave frequency of 4 MHz, which is obtained by using electronic circuits, that are well known and consequently not described here for the sake of brevity.

The voltage sine wave available at the output 41 of the generator 4 is preferably a distorted sine wave and consequently with harmonics at least of the first, second and third order.

The power of the generator 4 is adjusted so that the current available at the tip of each electrode 1 comes between 2 and 2.5 mA.

When the tip of each needle is rested on the surface 51 of the organic tissue 5, contact between the tip of each needle 1 and the organic tissue enables the passage of a current of around 2-2.5 mA, as mentioned previously.

Said current transmits an energy to the surrounding molecules that corresponds (as demonstrated experimentally) to what is called "molecular resonance".

This energy is just enough to break the bonds between the molecules affected by the passage of the current, while in the surrounding area it causes no breakdown, tearing, necrosis, reduction or increase in thickness, change in fluid content fluid, coagulation or other tissue degeneration.

Basically, this opening created in the molecular bonds equates to the creation of a tiny hole that, in practical terms, is the same diameter as each needle 1, i.e. around 50-55 μm.

Of course, needles of a different, larger or smaller gauge may be used, provided that the user bears in mind that the minimum gauge of the needle cannot be smaller than the diameter of the cells used for revitalisation.

The holder 20 of the array of needles 3 is then pushed in the direction in which the needles point and proceeds at a sufficiently slow pace such that, as the needle moves forward, the tip of the needle finds the hole already created by the flow of current and the consequent rupture of the molecular bonds.

It is easy to see that there is consequently no tearing of the connective tissue, and that a narrow hole corresponding to the gauge of the needle being inserted is consequently achieved.

As explained previously, this is particularly important and useful because the cells that are reimplanted on the tissue can thus penetrate in depth throughout the tissue and become grafted onto the walls of the holes, where they can multiply and very quickly revitalise the full thickness of the organic tissue.

Figure 1:
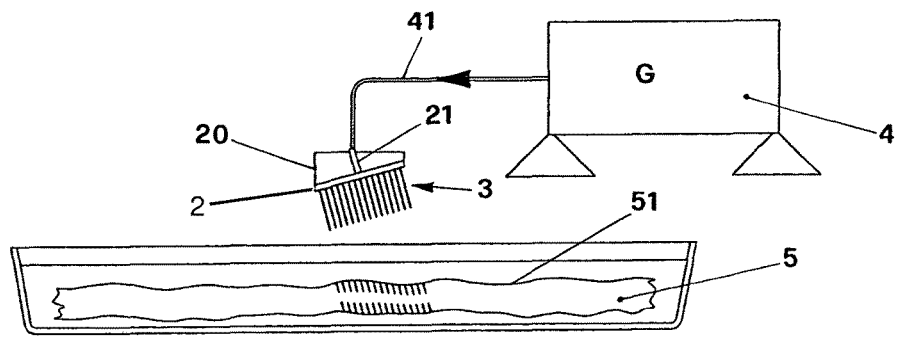
FIG. 1 shows a schematic cross-section of the device comprising a holder with an array of needles resting an the thickness of the tissue being prepared for revitalisation.

As shown in FIG. 1, the needles 1 penetrate preferably but not necessarily obliquely to the surface 51 of the scaffold 5, in order to increase the length of the holes and consequently obtain the maximum channelling effect in the scaffold.

Experiments have demonstrated that a 60° angle with respect to the vertical is more effective in the revitalisation process because the resulting holes are longer than the thickness of the scaffold.

Laboratory tests have shown that a useful dimension of the array of needles 3 containing the needles 1 is around 1 cm², with said array comprising approximately 200 needles; in this case, the current delivered by the generator 4 is no more than 500 mA.

The perforation procedure must naturally be repeated all over the surface 51 of the scaffold in order to obtain a homogeneous distribution of the holes throughout the thickness and over the entire useful surface of the tissue for transplantation.

Figure 4:
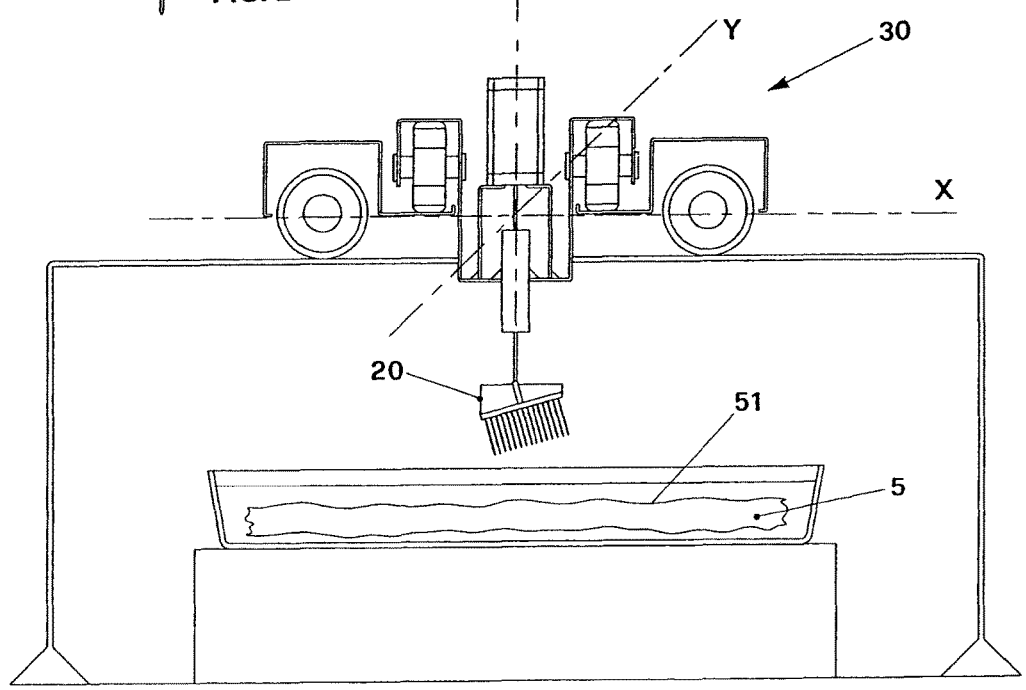
FIG. 4 shows a schematic view of the device for displacing the needle holder.

For this purpose, the invention uses a device for making the holes that is advantageously provided with means 30 for displacing the holder 20 along three Cartesian axes, i.e. along the vertical, or oblique axis Z, and along the Cartesian axes X and Y parallel to the plane of the surface 51 and shown schematically in FIG. 4.

Once the holes have been made in a given part of the scaffold 5, the holder 20 can be moved and the procedure can be repeated in an orderly manner so as to cover the entire surface 51.

Clearly, if the holder 20 carrying the array of needles 3 is connected to programmable displacement means 30, e.g. with stepping motors governed by an electronic control unit, the procedure can be repeated automatically and sequentially, and with the utmost precision.

After completing the series of holes in the acellular tissue 5, as explained above, it is evident that said acellular tissue can be placed in a Petri dish, or similar container, where the living cells can then be added, which are generally stem cells from the host individual intended to receive the graft.

Suitably nourished with a culture broth, said stem cells can quickly and easily occupy all the holes made by the needles 1, thereby ensuring a complete and effective revitalisation of the entire tissue for transplantation.

It is clear that the method of the invention achieves all the set objects of the invention, since a perfect and effective revitalisation is ensured and any risk of failure of the subsequent transplantation is prevented.

Moreover, the revitalisation process takes place much more rapidly than when the known technique is used, and with extremely successful results.

Where technical features mentioned in any claim are followed by reference signs, those reference sings have been included for the sole purpose of increasing the intelligibility of the claims and accordingly such reference signs do not have any limiting effect on the interpretation of each element identified by way of example by such reference signs.

I claim:

1. A method for preparing an acellular organic tissue for revitalisation by means of reimplantation of living cells, comprising:
    preparing said acellular tissue on an essentially flat surface; and
    creating a plurality of holes on a surface of said tissue, distributed over said surface of said tissue and positioned so that they penetrate at least through a portion of a thickness of said tissue, said holes being suitable for containing said living cells when they are reimplanted,
    wherein said plurality of holes is created by means of one or more metal needles connected to an electric power supply that induces, on a tip of each needle, the passage of a current of such intensity and wave form as to provide sufficient energy to break the bonds between the molecules comprising the organic tissue in the vicinity of the tip of said one or more needles, each hole being created by said passage of current and being large enough for the tip of said one or more needles to enter the space created by the opening of said molecular bonds.

2. The method according to claim 1, wherein said one or more metal needles are powered electrically with an alternating current of sine wave type with a frequency of approximately 4 MHz.

3. The method according to claim 2, wherein said electric power supply to said one or more needles has harmonics at least up to the third order.

4. The method according to claim 2, wherein an electric voltage is applied to said one or more needles of 200-230 Volts.

5. The method according to claim 2, wherein the current applied to each one or more needles is 2-2.5 mA.

6. The method according to claim 1, wherein a depth of said holes corresponds to a full thickness of said organic tissue.

7. The method according to claim 1, wherein a length of said holes is greater than the thickness of said acellular organic tissue.

8. The method according to claim 7, wherein said plurality of holes lie obliquely to the surface of said organic tissue.

9. The method according to claim 1, wherein said plurality of holes lie in a direction essentially perpendicular to the surface of said tissue.

10. The method according to claim 1, wherein the plurality of holes for revitalising said tissue are produced using a device comprising:
    said one or more metal needles arranged in a holder.

11. The method according to claim 10, wherein said electric power supply consists of a generator of sine wave voltage at a frequency of approximately 4 MHz.

12. The method according to claim 10, wherein said holder is suitable for creating an array of rows of needles essentially parallel to one another, said needles being substantially equidistant from one another.

13. The method according to claim 12, wherein said needles are arranged essentially perpendicular with respect to said holder.

14. The method according to claim 12, wherein said holder is positioned obliquely to the surface of the organic tissue being perforated.

15. The method according to claim 10, wherein a gauge of said one or more needles is at least 50-55 um.

16. The method according to claim 10, wherein a gauge of said one or more needles is greater than a maximum dimension of said living cells.

17. The method according to claim 10, wherein said device comprises means for displacing said one or more needles along at least one axis incident to the surface of said tissue and along at least one axis parallel to said surface of said organic tissue.

18. The method according to claim 17, wherein said displacement means induce a movement along two Cartesian axes lying essentially parallel to the surface of said organic tissue.

* * * * *